(12) United States Patent
Haff

(10) Patent No.: US 7,860,214 B1
(45) Date of Patent: Dec. 28, 2010

(54) CORRECTION OF X-RAY IMAGES

(75) Inventor: Ronald P Haff, Davis, CA (US)

(73) Assignee: The United States of America as represented by Secretary of Agriculture, Washington, DC (US)

( * ) Notice: Subject to any disclaimer, the term of this patent is extended or adjusted under 35 U.S.C. 154(b) by 83 days.

(21) Appl. No.: 12/138,380

(22) Filed: Jun. 12, 2008

Related U.S. Application Data

(60) Provisional application No. 60/934,531, filed on Jun. 13, 2007.

(51) Int. Cl.
*G01N 23/02* (2006.01)
(52) U.S. Cl. .......................... 378/58; 378/57
(58) Field of Classification Search ................... 378/57, 378/58
See application file for complete search history.

(56) References Cited

U.S. PATENT DOCUMENTS

| | | | | |
|---|---|---|---|---|
| 2,139,098 | A * | 12/1938 | Raney | 378/155 |
| 4,163,991 | A * | 8/1979 | Burrig | 378/57 |
| 6,614,878 | B2 * | 9/2003 | Bogatu et al. | 378/157 |
| 7,034,313 | B2 * | 4/2006 | Hoffman | 378/19 |
| 2002/0191738 | A1 * | 12/2002 | Mazess et al. | 378/57 |

OTHER PUBLICATIONS

Bull, C.R. and R. Zwiggelaar, "Discrimination between Low Atomic Number Materials from their Characteristic Scattering of X-ray Radiation" (1997) J. Agric. Engng Res. 68: 77-87.
Bull, C.R., R. Zwiggelaar, and R.D. Spelleer, "Review of Inspection Techniques base don the Elastic and Inelastic Scattering of X-rays and their Potential in the Food and Agricultural Industry" (1997) J. of Food Engineering 33: 167-179.
Butz, P., C. Hofmann, and B. Tauscher, "Recent Developments in Noninvasive Techniques for Fresh Fruit and Vegetable Internal Quality Analysis" (2005) J. of Food Science 70(9): 131-141.
Chen, X. et al. "Real Time Detection of Physical Hazards in De-Bonded Poultry Using High Resolution X-Ray Imaging" (2003) ASAE Meeting Paper No. 033084 St. Joseph, Mich.: ASAE.
Graves, M., A. Smith and B. Batchelor "Apporaches to Foreign Body Detection in Foods" (1998) Trends in Food Science & Technology 9: 21-27.
Graves, M., B. Batchelor and S. Palmer "3D X-ray Inspection of Food Products" (1994) SPIE 2298: 248-259.

(Continued)

*Primary Examiner*—Chih-Cheng G Kao
(74) *Attorney, Agent, or Firm*—Howard V. Owens; John D. Fado

(57) ABSTRACT

A technique to correct deficiencies in x-ray images of cylindrical or spherical objects that are a consequence of the geometry of the sample is disclosed, for both normal imaging of stationary objects with film or digital detectors and linescan imaging of moving objects. The methods described involve the use of attenuators specifically shaped to equalize the x-ray absorption across the sample, thus correcting the variation in pixel intensity caused by the varying thickness of the sample.

14 Claims, 6 Drawing Sheets

OTHER PUBLICATIONS

Haff, R.P "Real-Time Correction of Distortion in X-Ray Images of Cylindrical or Spherical Objects and its Application to Agricultural Commodities" (2008) American Society of Agricultural and Biological Engineers 5(1): 341-349.

Haff, R.P. and T.F. Schatzki "Image Restoration of Line-Scanned X-Ray Images" (1997) Opt. Eng. 36(12): 3288-3296.

Jayas, D.S., C. Karunakaran and J. Paliwal "Grain Quality Monitoring Using Machine Vision and Soft X-Rays for Cereal Grains" (2004) International Quality Grains Conference Proceedings.

Jha, S.N. and T. Matsuoka "Non-Destructive Techniques for Quality Evaluation of Intact Fruits and Vegetables" (2000) Food Sci. Technol. Res. 6(4): 248-251.

Korgher, C.M., J.G. Bartle, J.G. West and V.-H. Tran, "Digital X-ray Imaging and Image Processing for Object Detection in Closed Containers" (2004) Proceedings of the Computer Graphics and Imaging Conference, Kauaii, HI.

Lin, T.-T. et al. "An Adaptive Image Segmentation Algorithm for X-Ray Quarantine Inspection of Selected Fruits" (2005) ASAE Meeting Presentation Paper No. 05123. St. Joseph, Mich.: ASAE.

Martens, G. et al. "Coherent X-Ray Scatter Imaging for Foodstuff Contamination Detection" (1993) SPIE 2092: 387-398.

Schatzki, T.F. et al. "Defect Detection in Applies by Means of X-Ray Imaging" (1997) American Society of Agricultural Engineers 40(5): 1407-1415.

Schatzki, T.F., A. Grossman and R. Young "Recognition of Agricultural Objects by Shape" (1983) IEEE Transactions on Pattern Analysis and Machine Intelligence PAMI-5(6): 645-653.

Schatzki, T.F. et al. "Defect Detection in Apples by Means of X-Ray Imaging" (1996) SPIE 2907: 176-185.

Shahin, M.A., E.W. Tollner and S.E. Prussia "Filter Design for Optimal Feature Extraction from X-Ray Images" (1999) American Society of Agricultural Engineers 42(6): 1879-1887.

Talukder, A. et al. "A New Feature Extraction Method for Classification of Agricultural Products from X-Ray Images" In: Precision Agriculture and Biological Quality, SPIE Proceedings (Eds) G.E. Meyer and J.A. DeShazer (1998) vol. 3543 p. 53-64.

Tao, Y. And J.G. Ibarra "Thickness-Compensated X-Ray Imaging Detection of Bone Fragments in Deboned Poultry-Model Analysis" (2000) American Society of Agricultural Engineers 43(2): 453-459.

Wagner, G.G. "Combining X-Ray Imaging and Machine Vision" (1987) Optics, Illumination, and Image Sensing for Machine Vision II, SPIE Proceedings, Bellingham Washington.

Zwiggelaar, R., C.R. Bull and M.J. Mooney "X-ray Simulations for Imaging Applications in the Agricultural and Food Industries" (1996) J. Agric. Engng. Res. 63: 161-170.

Zwiggelarr, R. et al. "The Detection of 'Soft' Materials by Selective Energy X-ray Transmission Imaging and Computer Tomography" (1997) J. Agric. Engng. Res. 66: 203-212.

* cited by examiner

CORRECTION OF X-RAY IMAGES

This application claims priority benefit to U.S. Provisional Patent Application Ser. No. 60/934,531, filed Jun. 13, 2007.

BACKGROUND OF THE INVENTION

X-ray imaging has become a common tool for the inspection of agricultural commodities for defects, contaminants, and quality. Linescan x-ray units are replacing metal detectors in many processing plants because of their ability to detect non-metallic materials such as bones, glass, or rocks. While their use at present is mainly limited to the inspection of packaged food products, including canned foods and product packaged in jars, substantial research has been conducted in an effort to make real time x-ray inspection of fresh produce practical.

Schatzki et al. (1997) demonstrated the feasibility of detection of insect infestation and core rot in apples using a linescan x-ray system, although image quality was a major deterrent to detection of insects at the earlier life stages. Kim and Schatzki (2000) developed an algorithm that detected watercore damage in linescan x-ray images of apples. Tollner et al. (1992) used x-ray density as a measure of water content in apples and Talukter et al. (1998) developed algorithms for separation of agricultural commodities in x-ray images. In addition, x-ray inspection is a commonly used tool for quality control sampling of many agricultural products.

Despite this considerable research effort, real-time x-ray inspection of fresh produce is still uncommon in the industry, mainly because of limitations in image quality when using high-speed systems. Poor x-ray image quality is the main limiting factor for high-speed real time detection of many defects in fresh produce.

X-ray images of agricultural commodities often contain a deficiency that is a consequence of the round shape of the product being inspected. This is particularly true for the majority of fruit, as well as product packaged in jars and cans. Since it is necessary to apply enough x-ray energy to penetrate the thickest part of the sample, the thinner edges are often saturated and washed out in the x-ray image. The result is an image that is light in the center and becomes gradually darker towards the edges.

Alternatively, if the incident x-ray energy is reduced to allow imaging of the edges, there is often insufficient energy to penetrate the middle portion of the sample. While this is generally not a problem in identifying metal contaminants, which for the most part absorb all incident x-rays, less dense contaminants such as wood, bone, and even glass may not be detected because of this phenomenon if they are situated along the edges of the sample.

In order to compensate for the variation in pixel intensity across the image, it is common practice to normalize the image through a software correction. This is useful when automatic recognition algorithms are used to drive a rejection mechanism, as the algorithms can be affected by the lack of uniformity of image brightness. However, software corrections cannot recover information lost in the imaging process, such as the presence of a small object with low density situated along the edge of the sample that has been washed out due to saturation of the detectors.

A physical correction applied at the time of imaging would improve the overall image quality as well as increase the probability of detecting such contaminant.

SUMMARY OF THE INVENTION

It is therefore an object of the present invention to make use of attenuators to correct certain deficiencies that arise in x-ray images of spherical and cylindrical objects as a consequence of the varying thickness of sample material traversed by the x-ray beam.

Another object of the present invention is the identification of shapes for appropriate attenuators and their applications for normal x-ray imaging of stationary objects and for linescan imaging of moving objects. Application of the attenuators improves image quality, especially along the edges, and aids in the detection of unwanted defects or contaminants that might otherwise be missed.

BRIEF DESCRIPTION OF THE DRAWINGS

FIG. 4b is a side view showing a cross section of the arrangement in FIG. 4a.

LIST OF REFERENCE NUMERALS

1. X-ray source

DEFINITIONS

Figure 1:
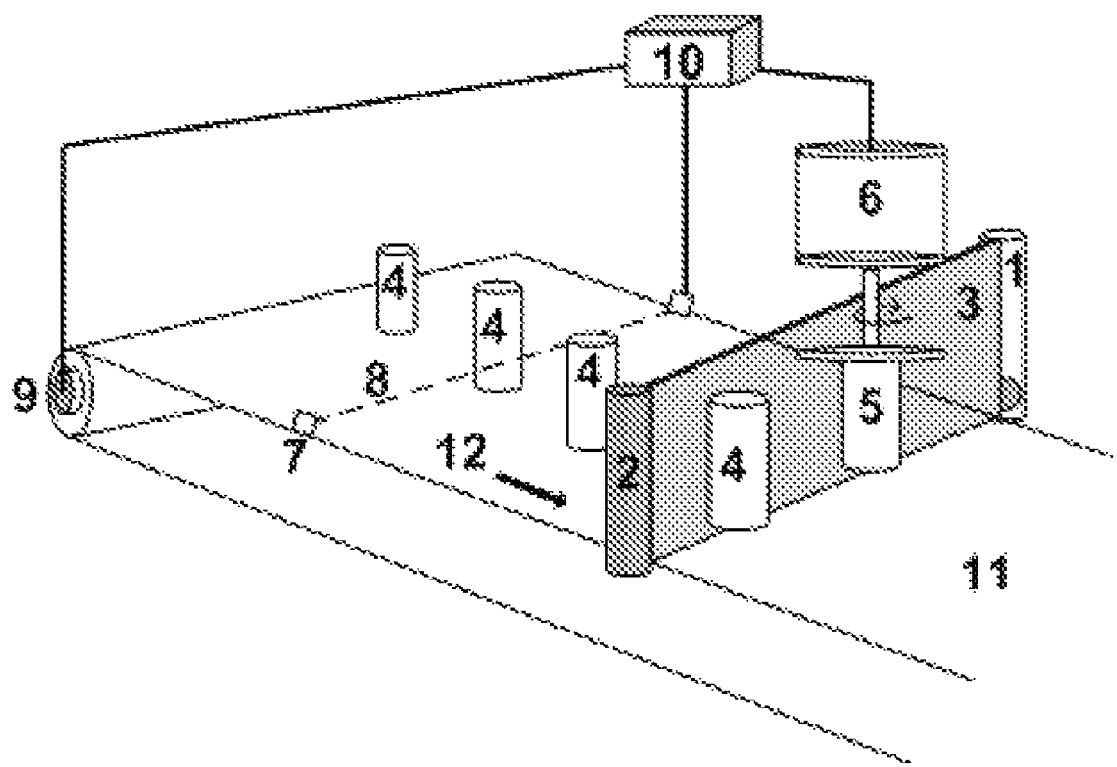
FIG. 1 illustrates an arrangement for incorporating a correcting attenuator for imaging cylindrical specimens on a line scan x-ray machine.

"Attenuator" means an object placed in the path of the x-ray beam with the specific purpose of reducing the x-ray intensity at the detectors.

"Dectector" means any object or device that produces a response to incident x-rays that is proportional to the intensity of the incident radiation.

"Microcontroller" means any instrument that uses a microprocessor to collect and analyze external data.

"Sphere" is defined by an object obeying the Cartesian coordinates $x^2+y^2+z^2=r^2$, where x, y, and z are the spatial axis of the coordinate system and r is the radius of the sphere. The term sphere also encompasses samples which possess regions embodying a circular cross section.

"Cylinder" means a solid of circular cross section in which the centers of the circles all lie on a single line, wherein the cross sections lie directly on top of each other. The term is inclusive of right circular cylinders.

"Normal" x-ray imaging refers to the capturing of an x-ray image of a stationary object using either film or a two dimensional array of digital detectors.

"Linescan" x-ray imaging refers to the capturing of an x-ray image of an object by repeated scanning of a one dimensional array of digital solid state detectors as the object moves through the plane of the x-rays. The image is constructed by combining the multiple one dimensional scans.

X-ray absorption coefficient refers to a measure of the ability of a material to absorb x-rays.

DETAILED DESCRIPTION OF THE INVENTION

According to an embodiment of the invention herein is described a method for correcting deficiencies in x-ray images of cylindrical or spherical objects for both normal and linescan two dimensional imaging. In accordance with this embodiment the method describes attenuators appropriately shaped to equalize the x-ray absorption across the width of the sample, thus correcting the variation in pixel intensity caused by varying sample thickness In further accordance with this embodiment formation of the two dimensional image can occur through either linescan or normal two dimensional imaging. For line scan imaging a series of one dimensional scans are reconstructed to form the image of the specimen, wherein the attenuator thickness is varied as the sample passes through the plane of the x-rays, either by rotation or linear actuation. In the direct method, the two dimensional x-ray imaging occurs wherein the entire specimen is imaged at one time, without reconstruction of one dimensional scans.

An embodiment of the invention allows for removing the deficiencies in x-ray images of any unprocessed fruits or vegetables possessing a circular cross sectional area, including but not limited to apples, oranges, limes, lemons, peaches, apples, nectarines, plums, avocados, etc. Additionally, other non agricultural spherical objects may be imaged such as ball bearings, may be imaged.

A further embodiment of the invention allows for removing deficiencies in x-ray images of canned goods containing food or non-food products.

The attenuator is designed with the appropriate shape and x-ray absorption coefficient to equalize x-ray attenuation across a cylindrical or spherical specimen. Since each object to be imaged may vary in composition, the attenuator material may be composed of natural (derived from plant or animal source) polymers, synthetic polymers or mixtures and derivatives thereof to maximize the x-ray absorption coefficient. The term "natural polymer" is meant to include within its meaning such polymers which have been modified by various processing steps, from the natural state. In this context, the processing steps may be chemical, biochemical, or mechanical steps.

Herein the term "synthetic polymer" and variants thereof, without more, is meant to have its ordinary meaning in the polymer art; i.e., a non-natural polymer typically prepared by polymerizing smaller molecules. Synthetic polymers may include but are not limited to Acrylonitrile-Butadiene-Styrene, Allyl Resin, Epoxy, Ethylene vinyl alcohol Fluoroplastics, Ionomer, Liquid Crystal Polymer, Melamine formaldehyde, Phenol-formaldehyde Plastic, Polyacetal, Polyacrylates, Polyacrylonitrile, Polyamide, Polybutadiene, Polybutylene, Polycarbonate, Polydicyclopentadiene, Polyektone, Polyester, Polyetheretherketone, Polyetherimide, Polyethersulfone, Polyethylene, Polyethylenechlorinates Polyimide, Polymethylpentene, Polyphenylene Oxide, Polyphenylene Sulfide, Polyphthalamide, Polypropylene Polystyrene, Polysulfone, Polyurethane, Polyvinylchloride, Polyvinylidene Chloride, Silicone, and Thermoplastic elastomers.

a) Linescan Imaging of Cylindrical Objects

Referring to FIG. 1, a rotating correcting attenuator 5 is incorporated into the x-ray plane 3 of a linescan x-ray system consisting of an x-ray source 1, a linear array of x-ray detectors 2, and a conveyor belt 11 which transports the specimens 4, which in this arrangement are assumed to have a cylindrical shape. As a specimen 4 passes through the x-ray plane 3 the attenuator 5 rotates through an angle of 180 degrees. The attenuator 5 has a shape that is designed to equalize the x-ray intensity sensed at the detectors 2 and thus compensates for the variation in pixel intensity that is a consequence of the varying thickness of the specimen 4. Timing of the rotation of the attenuator 5 with the passing of the specimen 4 is accomplished through the use of an encoder 9, an optical switch 7, and a microprocessor 10.

Figure 2A:
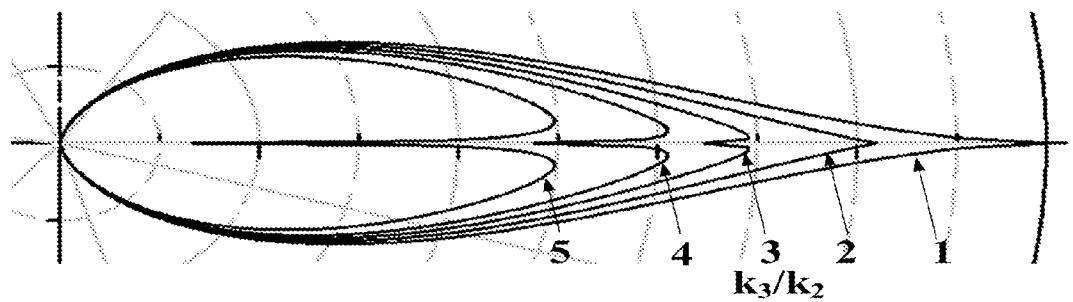
FIGS. 2A and 2B show a polar plot of the required cross section for a rotating attenuator in a linescan system with $k_1=k_2$ and the ratio $k_3/k_2$ varying through values of 0 (no container), 1, 2, 3, and 5.
Figure 2B:
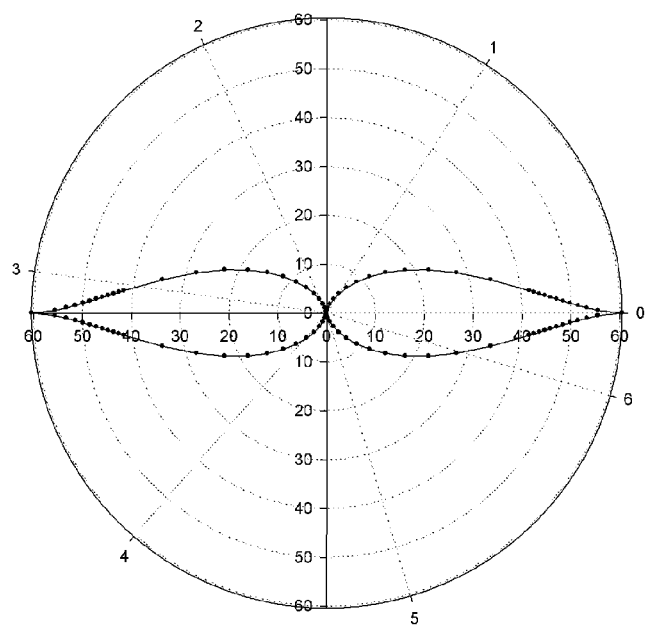

The microprocessor 10 translates the revolutions of the encoder 9 driven by the belt gear into speed of the specimen 4 along the direction of belt motion 12, and the breaking of the optical beam 8, generated by the optical switch 7 provides the distance between the specimen 4 and the x-ray plane 3, allowing the microprocessor 10 to transmit the proper delay before rotation of the attenuator 5 as well as the rotation speed. The required shape of the cross section for the attenuator 5 is given here in the general case where the specimen is enclosed in a container:

$$t(\beta) = \frac{1}{k_2}\left\{2k_3\left[dR - \sqrt{R_0^2 - R_i^2\cos^2\theta} + R_i\sin\theta\right] + 2k_1R_i(1 - \sin\theta)\right\} \quad (1)$$

where t is the radial variable in polar coordinates, k1, k2, and k3 are the x-ray absorption coefficients of the specimen 4, the attenuator 5, and the container respectively, $R_i$ is the inside radius of the container, dR is the thickness of the container, and $$\theta = \cos^{-1}\left(1 - \frac{2\beta}{\pi}\right) \quad (2)$$

with β being the angular variable. The first term corrects for the variation in thickness of the cylindrical specimen 4 as it cuts through the x-ray plane 3, while the second terms corrects for the variation in thickness of the container. FIGS. 2a and 2b show a polar plot of the representative attenuator shapes (consistent with equation 1) that maximize attenuation of the x-ray signal across a cylindrical object.

b) Linescan Imaging of Spherical Objects

Figure 3:
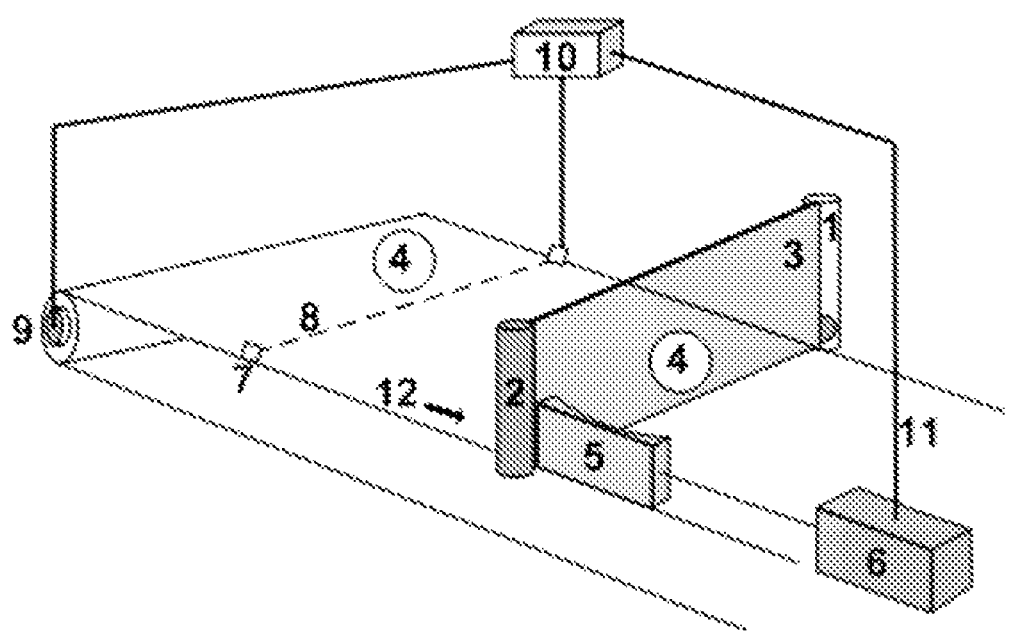
FIG. 3 illustrates the arrangement for applying a correcting attenuator to spherical samples on a linescan x-ray system.

Referring to FIG. 3, a correcting attenuator 5 is introduced into the x-ray plane 3 of a linescan x-ray system as described above through means of a linear actuator 6, where for this arrangement the specimen 4 is assumed to have a spherical shape. The encoder 9, optical switch 7, and the microcontroller 10 again provide the correct timing for activation of the linear actuator 6. The required shape of the attenuator 5 is given by:

$$t(x) = \frac{2k_1}{k_2}\left(R - \sqrt{R^2 - x^2}\right), \quad (3)$$

where R is the radius of the specimen 4 and x is the distance from the center of the attenuator 5. For the special case of $k_2=2k_1$ the shape matches the curvature of the specimen.

Figure 4A:
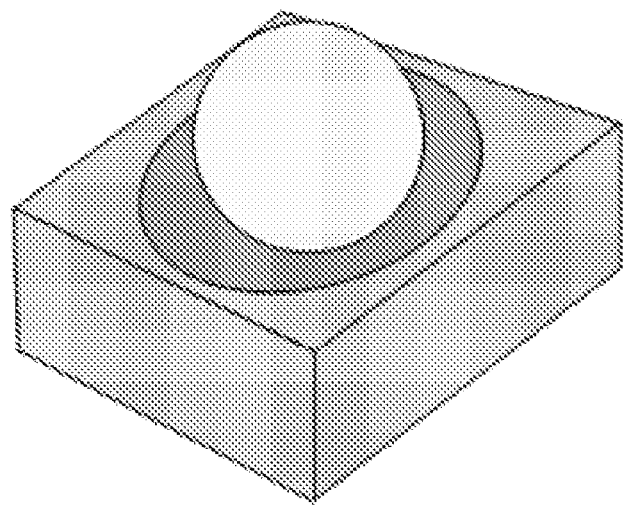
FIG. 4a illustrates an oblique view of the arrangement for applying a correcting attenuator for normal x-ray imaging of a stationary sphere.
Figure 4B:
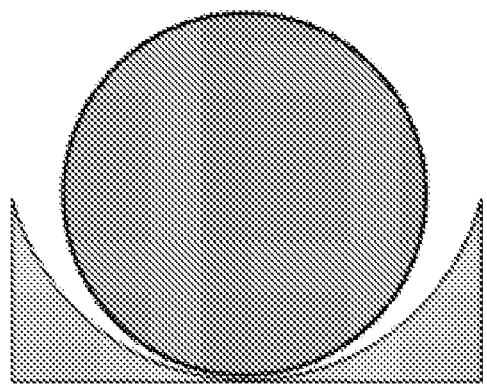

FIGS. 4a and 4b provide embodiments of attenuator shapes appropriate for spherical objects.

c) Normal Imaging of Spherical or Cylindrical Objects

Referring to FIG. 4a and FIG. 4b a correcting attenuator is placed between a spherical 4 or cylindrical 5 specimen and the detectors, which may be either film or a digital detector array. The required shape of the attenuator is given in equation 4. Equating equations 2 and 3, substituting the relations from equation 4, and solving for t gives the requirement for a uniform transmitted intensity as a function of the distance (x) from the center:

$$t(x) = \frac{2k_3}{k_2}\left(dR - \sqrt{R_o^2 - x^2} + \sqrt{R_i^2 - x^2}\right) + \frac{k_1}{k_2}\left(D - 2\sqrt{R_i^2 - x^2}\right) \quad (4)$$

where dR is the thickness of the container wall, D is the diameter of the sample, and $R_o$ and $R_i$ are the outer and inner radii of the container. Note that for the case of no container the first term vanishes as expected and $R_i$ is just the sample radius, giving the result of equation 3.

Example 1

Normal imaging of an apple, an orange, and a lime fruit were conducted to demonstrate the effectiveness of the technique described here. Additionally, a sample of modeling clay was tested for the ideal case of a simple sphere. For this study, all 2D x-ray images were obtained using a Faxitron x-ray cabinet (Faxitron Corp., Buffalo Grove, Ill.) with Kodak x-ray film. After developing, the film was digitized using a film scanner. The principles involved are applicable to real-time x-ray systems with digital detectors, and the results found here should apply equally to any type of x-ray system, with the exception of linescan systems, which will be discussed below.

Figure 5:
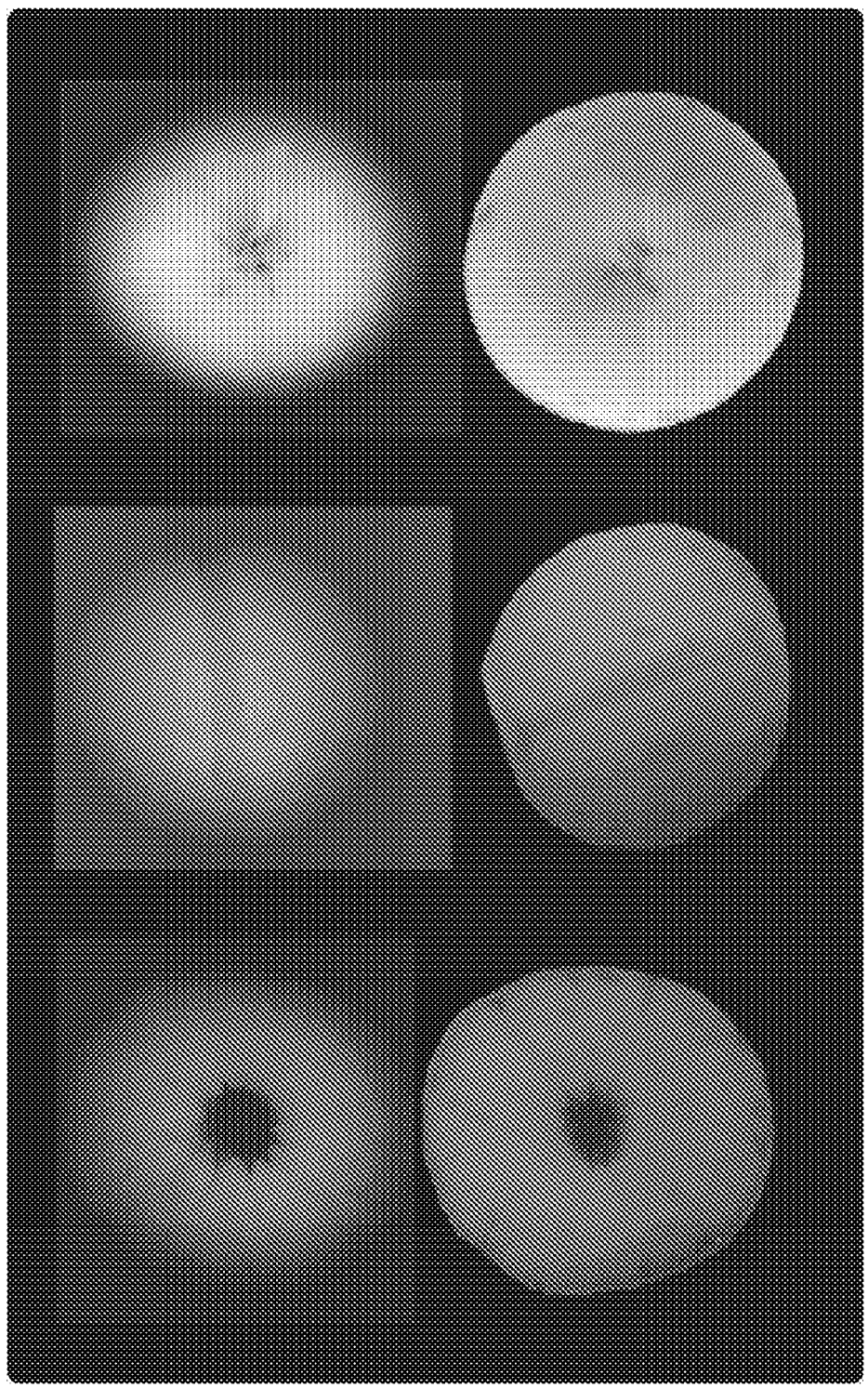
FIG. 5 shows x-ray images for the case of normal imaging of an apple, an orange, and a lime with (right) and without (left) the use of the correcting attenuator.

FIG. 5 shows x-ray images of the fruit with and without the use of the correcting attenuator.

Example 2

Linescan Imaging of can

Figure 6:
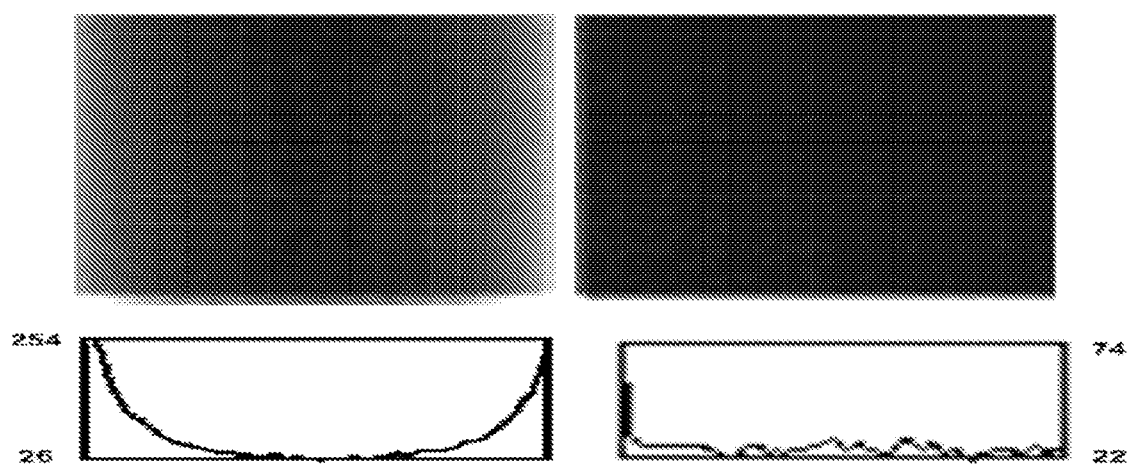
FIG. 6 shows linescan images of a cylinder with (right) and without (left) a correcting attenuator. The plots underneath each image show a pixel intensity profile for a horizontal slice across the corresponding image.

A rotating attenuator for a cylinder with a diameter of 57.16 mm (2.25 in.) mm and a height of 67.8 mm (2.67 in.) was constructed in the shape derived in equation 1 and shown in FIG. 2. Both the can and the attenuator were constructed from grey Polyvinylchloride (PVC). FIG. 6 shows x-ray images of the cylinder with and without the use of the correcting attenuator, along with plots of the pixel intensity profile.

I claim:

1. An x ray inspection apparatus comprising:
   a) A means for conveying a cylindrical or spherical object to a radiation source,
   b) an encoder for monitoring the conveyance of the object,
   c) a radiation source adapted to direct radiation along a path toward said object,
   d) a means for detecting entry of the object into the x ray plane,
   e) an attenuator with the appropriate shape and x-ray absorption coefficient to equalize x-ray attenuation across said object,
   f) a means for detecting the attenuated x ray signal,
   g) a microcontroller for synchronization of the encoder data and positioning of the attenuator.

2. The apparatus of claim 1, wherein the attenuator is rotated into the x ray path.

3. The apparatus of claim 2, wherein the appropriate shape of the attenuator is defined by the formula:

$$t(\beta) = \frac{1}{k_2}\left\{2k_3\left[dR - \sqrt{R_0^2 - R_i^2\cos^2\theta} + R_i\sin\theta\right] + 2k_1R_i(1 - \sin\theta)\right\}.$$

4. The apparatus of claim 1, wherein the attenuator is linearly positioned into the x ray path.

5. The apparatus of claim 4, wherein the appropriate shape of the attenuator is defined by the formula:

$$t(x) = \frac{2k_1}{k_2}(R - \sqrt{R^2 - x^2}),$$

where R is the radius of the object and x is the distance from the center of the attenuator.

6. The apparatus of claim 1, wherein the object is placed on top of the attenuator.

7. The apparatus of claim 1, wherein the object is cylindrical.

8. The apparatus of claim 1, wherein the object is spherical.

9. The apparatus of claim 4, wherein the spherical object is a fruit or vegetable possessing a circular cross section.

10. A method for correcting deficiencies in x-ray images of cylindrical or spherical objects comprising:
    a) Placing a sample on a conveyor for movement of the object to a radiation source,
    b) positioning an attenuator of the appropriate shape and x-ray absorption coefficient to equalize x-ray attenuation across a cylindrical or spherical object within the x ray path,
    b) irradiation of the object with a radiation source adapted to direct radiation along a path toward said object,
    c) detecting and processing said attenuated signal to form a 2 dimensional image.

11. The method of claim 10 wherein the attenuator is positioned, between the object and the detector.

12. The method of claim 11 wherein the attenuator is linearly positioned into the x ray path between the object and the detector.

13. The method of claim 11, wherein the attenuator is rotated into the x ray path between the object and the detector.

14. The method of claim 10 wherein the attenuator is positioned, between the object and the conveyor.

* * * * *